(12) United States Patent
Lee et al.

(10) Patent No.: US 12,178,714 B2
(45) Date of Patent: Dec. 31, 2024

(54) SPLIT INSERTION-TYPE INTERVERTEBRAL CAGE

(71) Applicants: Sang Ho Lee, Seoul (KR); Sang Hyeop Jeon, Busan (KR); Jun Seok Bae, Seoul (KR); Young Sik Bae, Seoul (KR)

(72) Inventors: Sang Ho Lee, Seoul (KR); Sang Hyeop Jeon, Busan (KR); Jun Seok Bae, Seoul (KR); Young Sik Bae, Seoul (KR)

(73) Assignee: Sang Ho Lee, Seoul (KR)

( * ) Notice: Subject to any disclaimer, the term of this patent is extended or adjusted under 35 U.S.C. 154(b) by 266 days.

(21) Appl. No.: 17/626,232

(22) PCT Filed: Jul. 13, 2020

(86) PCT No.: PCT/KR2020/009171
§ 371 (c)(1),
(2) Date: Jan. 11, 2022

(87) PCT Pub. No.: WO2021/006713
PCT Pub. Date: Jan. 14, 2021

(65) Prior Publication Data
US 2022/0249246 A1    Aug. 11, 2022

(30) Foreign Application Priority Data
Jul. 11, 2019    (KR) .................... 10-2019-0083798

(51) Int. Cl.
*A61F 2/44*      (2006.01)
*A61F 2/30*      (2006.01)

(52) U.S. Cl.
CPC .... *A61F 2/4455* (2013.01); *A61F 2002/3008* (2013.01); *A61F 2002/30187* (2013.01);
(Continued)

(58) Field of Classification Search
CPC ...... A61F 2/442; A61F 2/4425; A61F 2/4455; A61F 2/446; A61F 2/4465;
(Continued)

(56) References Cited

U.S. PATENT DOCUMENTS

| | | |
|---|---|---|
| 9,687,356 B1 | 6/2017 | Spangler et al. |
| 2005/0154463 A1 | 7/2005 | Tries |

(Continued)

FOREIGN PATENT DOCUMENTS

| | | |
|---|---|---|
| CN | 106073953 A | 11/2016 |
| JP | 4920594 B2 | 4/2012 |

(Continued)

*Primary Examiner* — Eduardo C Robert
*Assistant Examiner* — Christina Negrellirodriguez
(74) *Attorney, Agent, or Firm* — NKL Law; Jae Youn Kim

(57) ABSTRACT

Provided is a cage to be inserted into vertebrae. The cage configured to reduce a risk of organs, muscles, and nerves being injured during an insertion surgery process and to allow the insertion surgery process to be easily performed. To this end, the present invention provides a cage including a leading insertion portion which is inserted from the front of vertebrae to be in position between the vertebrae and a following insertion portion which is coupled to one surface of the leading insertion portion to be in position between the vertebrae. According to the present invention, there are effects of reducing a risk of organs, muscles, and nerves being injured during a surgery process of inserting the cage, facilitating the surgery process of inserting the cage, reducing post-surgery side effects by stably fixing the cage, and reducing a surgery time to reduce a burden to a patient.

9 Claims, 15 Drawing Sheets

(52) U.S. Cl.
CPC .............. *A61F 2002/30191* (2013.01); *A61F 2002/30878* (2013.01); *A61F 2002/448* (2013.01)

(58) Field of Classification Search
CPC ........ A61F 2002/4445; A61F 2002/445; A61F 2002/448
USPC ........................................... 623/17.11–17.16
See application file for complete search history.

(56) References Cited

U.S. PATENT DOCUMENTS

| | | | |
|---|---|---|---|
| 2008/0039942 A1* | 2/2008 | Bergeron | A61F 2/442 623/17.16 |
| 2009/0005870 A1 | 1/2009 | Hawkins et al. | |
| 2010/0023128 A1* | 1/2010 | Malberg | A61F 2/442 623/17.16 |
| 2011/0320000 A1* | 12/2011 | O'Neil | A61F 2/30771 623/17.16 |
| 2013/0158664 A1 | 6/2013 | Palmatier et al. | |
| 2013/0184823 A1* | 7/2013 | Malberg | A61F 2/442 623/17.13 |

FOREIGN PATENT DOCUMENTS

| | | |
|---|---|---|
| KR | 10-1614561 B1 | 4/2016 |
| KR | 10-2017-0001989 A | 1/2017 |
| KR | 10-1794485 B1 | 11/2017 |
| KR | 10-1822632 B1 | 1/2018 |
| WO | 98/44877 A1 | 10/1998 |
| WO | 2006/116851 A1 | 11/2006 |

* cited by examiner

SPLIT INSERTION-TYPE INTERVERTEBRAL CAGE

TECHNICAL FIELD

The present invention relates to a cage to be inserted between vertebrae in a split form.

BACKGROUND ART

As conventional methods for inserting a cage, there are anterior insertion, lateral insertion, and posterior insertion.

Since organs are located in front of the spine, in order to insert a cage through the front, it is necessary to temporarily move the organs aside or to insert a cage through a space between the organs. Accordingly, since a risk of the organs being injured is present and it is necessary to move the main artery and main vein which are the largest blood vessels of the human body, surgery is difficult and dangerous, and thus a skilled medical specialist is required. Also, since nerves are located in the rear of the vertebrae and vertebral arches and vertebral protrusions are located on an insertion path of a cage, even when the cage is inserted through the rear, a risk of muscles and nerves being injured is present and it is necessary to remove a vertebra.

Also, the psoas muscles flank the spine, and tangled nerves heading for the legs pass through the psoas muscles. Accordingly, when a cage is inserted from the side, it is necessary to perform surgery while separating the psoas muscles bilaterally to expose the centrum space. In this process, there is a possibility of causing muscle damage and damage to the nerves to the legs.

RELATED ART DOCUMENTS

Patent Documents

Korean Patent Registration No. 10-1822632 (registered on Jan. 22, 2018)
Korean Patent Registration No. 10-1794485 (registered on Oct. 31, 2017)

DISCLOSURE

Technical Problem

The present invention is directed to providing a cage which is inserted in a split form.

The present invention is also directed to providing a cage capable of reducing a risk of organs, muscles, and nerves being injured during an insertion surgery process.

The present invention is also directed to providing a cage facilitating an insertion surgery process.

Technical Solution

One aspect of the present invention provides a cage to be inserted between a plurality of vertebrae. The cage includes a leading insertion portion which is inserted from the front of the vertebrae to be in position between the vertebrae and a following insertion portion which is coupled to one surface of the leading insertion portion to be in position between the vertebrae.

Advantageous Effects

According to the present invention, a risk of organs, muscles, and nerves being injured during a surgery process of inserting a cage is reduced.

Also, according to the present invention, the surgery process of inserting the cage is facilitated.

Also, according to the present invention, the cage is stably fixed so that post-surgery side effects can be reduced.

Also, according to the present invention, a surgery time is reduced to reduce a burden on a patient.

MODES OF THE INVENTION

The terms used herein will be described in brief, and one embodiment of the present invention will be described in detail. Although general terms used widely at present are selected as the terms used herein in consideration of functions in the present invention, these may vary according to the intentions of those of ordinary skill in the art, precedents, the advent of new technologies, and the like. Also, in particular cases, there are terms selected by the applicant. In such cases, the meaning thereof will be stated in detail in a corresponding description of the present invention. Accordingly, the terms used herein should be defined on the basis not of simple designations the terms, but of the meanings of the terms and the content throughout the present invention.

Hereinafter, an embodiment of the present invention will be described in detail with reference to the attached drawings.

Figure 1:
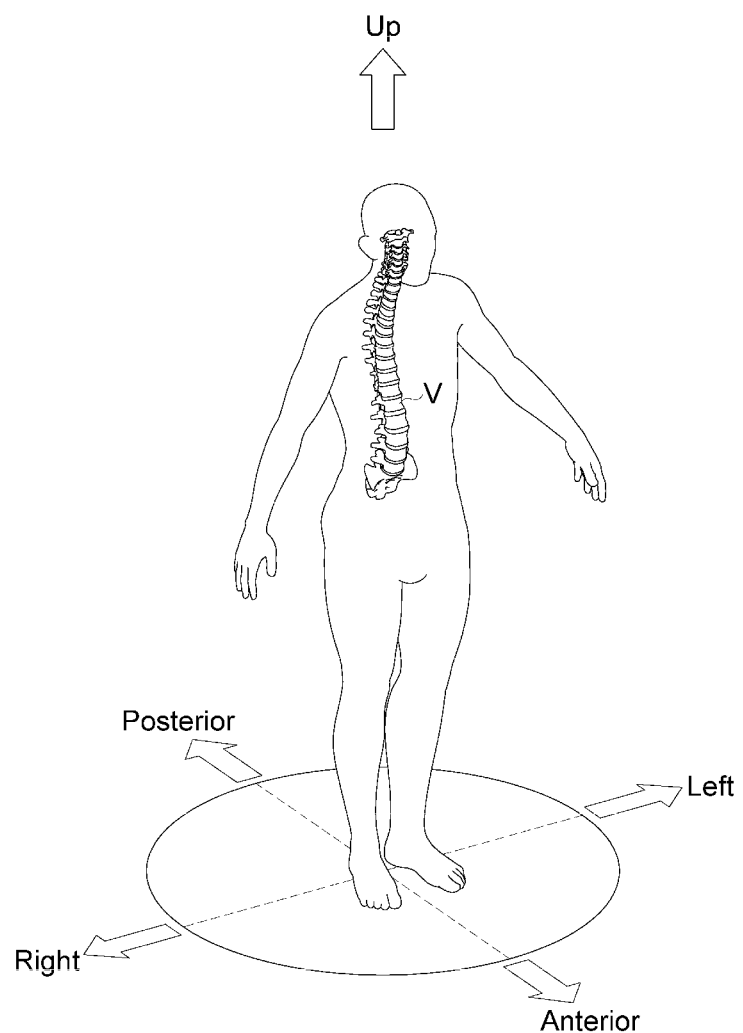
FIG. 1 is a view illustrating directional relationships used in the present invention.

FIG. 1 is a view illustrating directional relationships used in the present invention. In the description, the term "front" means a direction in front of the spine, and the term "rear" means a direction in the rear of the spine. That is, the front is an anterior direction, and the rear is a posterior direction. Also, throughout the present invention, "left" means a leftward direction of the spine, and "right" means a rightward direction of the spine. Also, in the description, "one side" means any one direction of the left side and the right side, and "the other side" means the direction opposite to the direction of the one side. Also, in the present invention, "up" means a direction toward the cranium on the basis of the spine, and "upper surface" means a surface facing upward. Likewise, "down" means a direction toward the coccyx on the basis of the spine, and "lower surface" means a surface facing downward.

Also, in the present invention, "insertion direction" means a direction in which a cage 10 according to the present invention is inserted between the vertebrae. The cage 10 according to the present invention has an insertion direction from the front to the rear of the spine.

Figure 2:
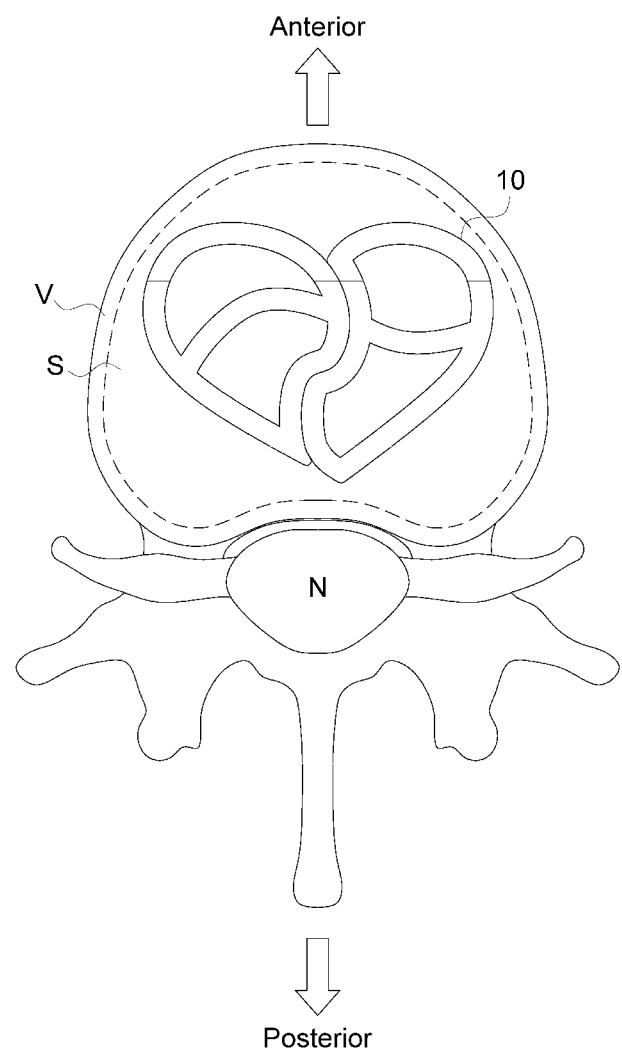
FIG. 2 is a plan view illustrating vertebrae and a cage according to one embodiment of the present invention.

FIG. 2 is a plan view illustrating vertebrae V and the cage 10 according to one embodiment of the present invention.

Originally, there are disks between the vertebrae V. Hereinafter, a space in which a disk is located normally is referred to as a centrum space S. Nerves N are located in the rear of the centrum space S.

When a failure occurs in a disk and thus the disk cannot perform its function appropriately, the cage 10 is inserted, replacing a part or an entirety of the disk, to support the vertebrae while maintaining an interval between the vertebrae. Here, a vertebra on an upper side which is supported by an upper surface of the cage 10 will be referred to as an "upper vertebra." Also, a vertebra on a lower side which is supported by a lower surface of the cage 10 will be referred to as a "lower vertebra." That is, a lower surface of an upper vertebra V1 comes into contact with and is supported by the upper surface of the cage 10, and an upper surface of a lower vertebra V2 comes into contact with and is supported by the lower surface of the cage 10.

Figure 3:
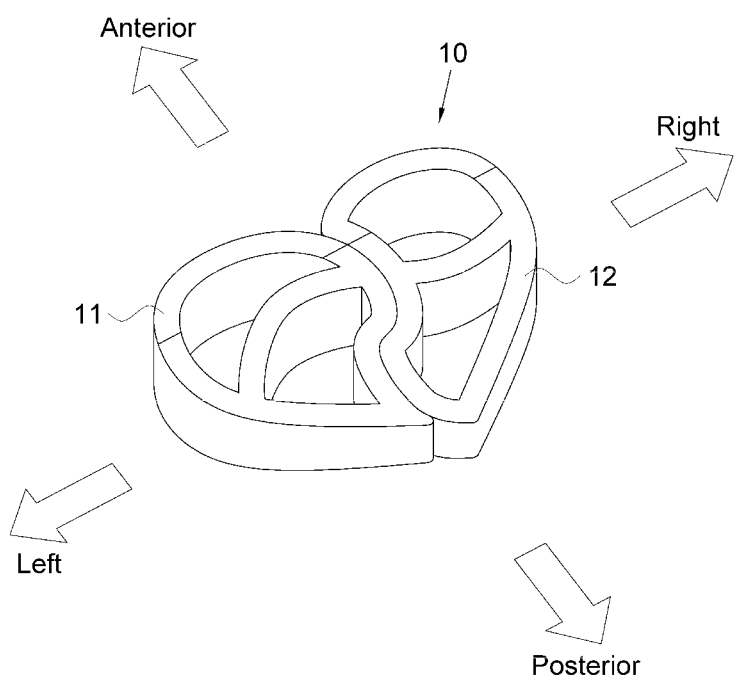
FIG. 3 is a perspective view illustrating the cage according to one embodiment of the present invention.

FIG. 3 is a perspective view illustrating the cage 10 according to one embodiment of the present invention.

As conventional surgeries for inserting a cage, there are anterior insertion, lateral insertion, and posterior insertion. However, since organs are located in front of the spine, in order to insert a cage through the anterior, it is necessary to temporarily move the organs aside or to insert a cage through a space between the organs. Accordingly, since a risk of the organs being injured is present and it is necessary to move the main artery and main vein which are the largest blood vessels of the human body, surgery is difficult and dangerous and thus a skilled medical specialist is required.

Also, since nerves are located in the rear of the vertebrae and vertebral arches and vertebral protrusions are located on an insertion path of the cage, even when the cage is inserted through the rear, a risk of muscles and nerves being injured is present and it is necessary to remove a vertebra.

Also, the psoas muscles flank the spine, and tangled nerves heading for the legs pass through the psoas muscles. Accordingly, when a cage is inserted from the side, it is necessary to perform surgery while separating the psoas muscle bilaterally to expose the centrum space S. In this process, there is a possibility of causing muscle damage and damage to the nerves to the legs.

The remedy this problem, the present invention provides a cage including a leading insertion portion 11 which is inserted from the front of the vertebrae V to be in position between the vertebrae V and a following insertion portion 12 coupled to one surface of the leading insertion portion 11 to be in position between the vertebrae V. Here, "in position" means at a position at which an exterior of the cage 10 corresponds to the centrum space S enough to support the vertebrae. That is, "in position" refers to a position at which the exterior of the cage 10 does not protrude from the centrum space S while coming into adequate contact with and supporting the upper vertebra V1 and the lower vertebra V2. The effects of the cage 10 being inserted in a separated form as the leading insertion portion 11 and the following insertion portion 12 include that it is easy to insert the cage 10 and for it to be in position after the insertion.

Figure 4:
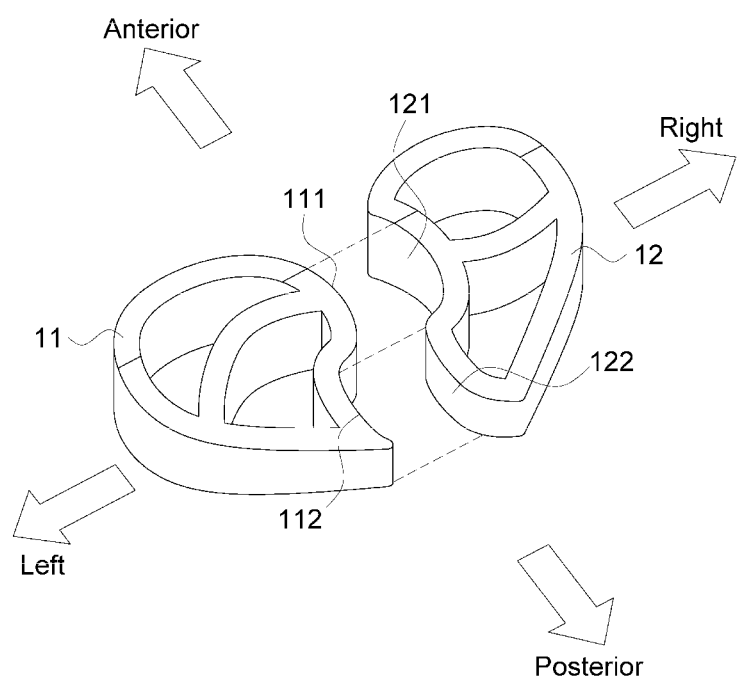
FIG. 4 is a perspective view illustrating a leading insertion portion and a following insertion portion according to one embodiment of the present invention.

FIG. 4 is a perspective view illustrating the leading insertion portion 11 and the following insertion portion 12 according to one embodiment of the present invention.

As an exemplary embodiment, the leading insertion portion 11 and the following insertion portion 12 may have cross-sectional shapes in which a width of one end in an insertion direction is smaller than a width of the other end. This makes it easier to insert the leading insertion portion 11 and the following insertion portion 12.

Also, since it is necessary to insert the cage 10 into a human body, when outer circumferential surfaces of the leading insertion portion 11 and the following insertion portion 12 are angular, organs, muscles, and nerves may be injured. Accordingly, the outer circumferential surfaces may be rounded without angular parts. In the embodiment, the outer circumferential surfaces of the leading insertion portion 11 and the following insertion portion 12 will be described on the basis of being curved.

As a more exemplary embodiment, a first curved surface 110 may be provided on the leading insertion portion 11 in one direction, and a second curved surface 120 may be provided on the following insertion portion 12 in the other direction.

As a more exemplary embodiment, the first curved surface 110 may include a first convex portion 111 formed to protrude in one direction and a first concave portion 112 formed to be adjacent to the first convex portion 111, and the second curved surface 120 may include a second concave portion 121 and a second convex portion 122 which correspond to the first convex portion 111 and the first concave portion 112, respectively. Providing the respective convex portions and concave portions makes it easier for an operating surgeon to combine the leading insertion portion 11 with the following insertion portion 12 by allowing the first curved surface 110 and the second curved surface 120 to correspond to each other.

Hereinafter, joining of the leading insertion portion 11 and the following insertion portion 12 according to one embodiment of the present invention will be described in detail with reference to FIGS. 5 to 8.

Figure 5:
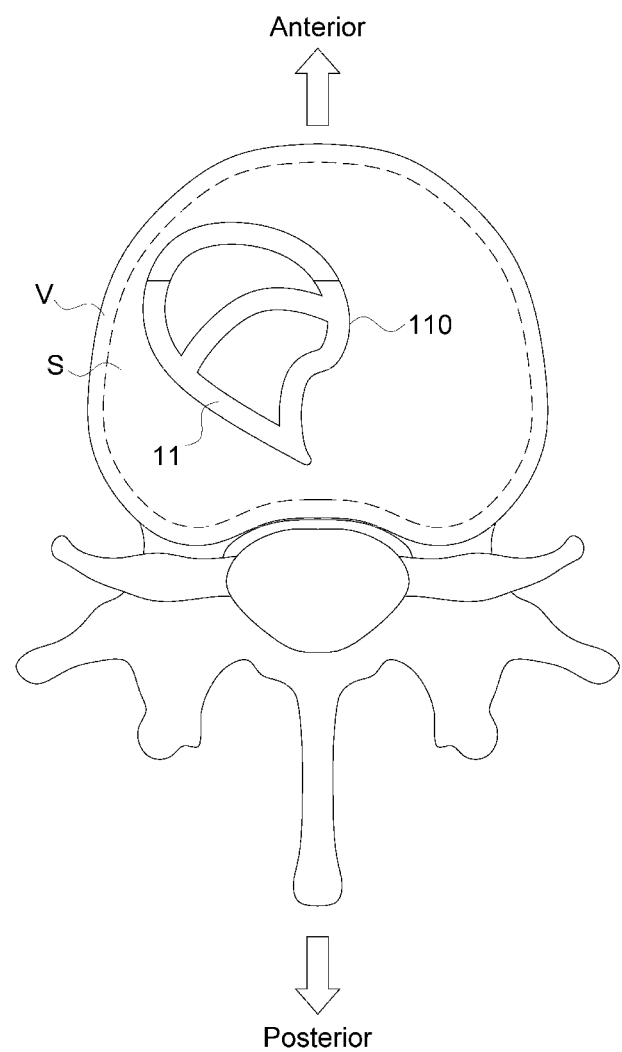
FIG. 5 is a plan view illustrating a state in which the leading insertion portion is in position between the vertebrae according to one embodiment of the present invention.

FIG. 5 is a plan view illustrating a state in which the leading insertion portion 11 is in position between the vertebrae V according to one embodiment of the present invention.

The leading insertion portion 11 is inserted between the vertebrae V while in position to leave a space in which the following insertion portion 12 will be positioned in the one direction in which the first curved surface 110 is formed.

That is, on the basis of a center of the centrum space S, the leading insertion portion 11 is in position in the other direction.

Figure 6:
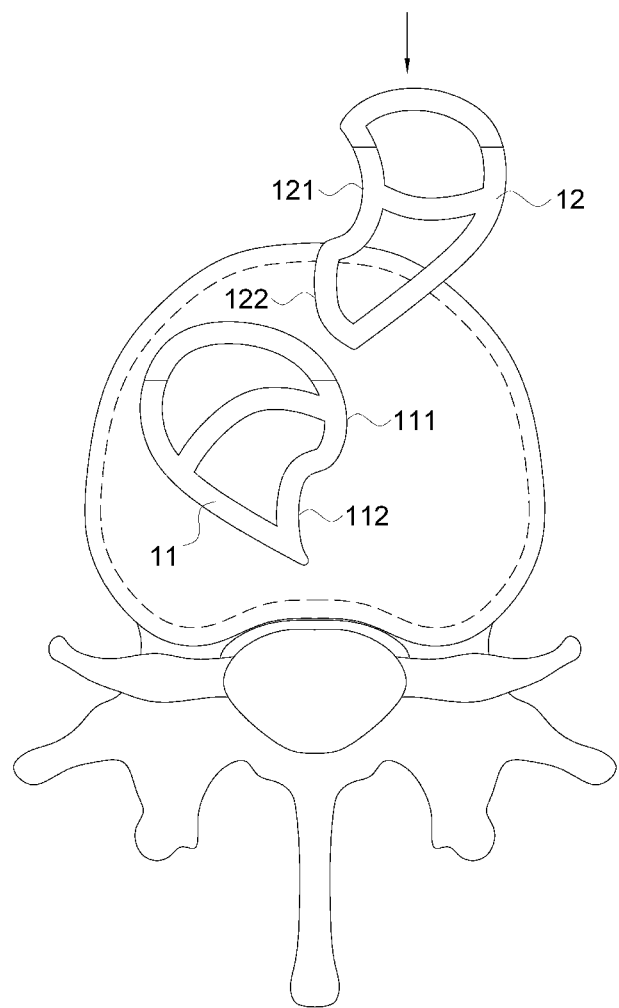
FIG. 6 is a plan view illustrating a state in which the following insertion portion is inserted between the vertebrae according to one embodiment of the present invention.

FIG. 6 is a plan view illustrating a state in which the following insertion portion 12 is inserted between the vertebrae V according to one embodiment of the present invention. The embodiment will be described on the basis that the first convex portion 111 is formed in a front part of the first curved surface 110 and the first concave portion 112 is formed in a rear part.

The following insertion portion 12 is inserted through the front of the vertebrae V while being inserted toward the part in the one direction on the basis of the center of the centrum space S. Accordingly, the second convex portion 122 comes into contact with the first convex portion 111 and is inserted while moving along the first convex portion 111.

Figure 7:
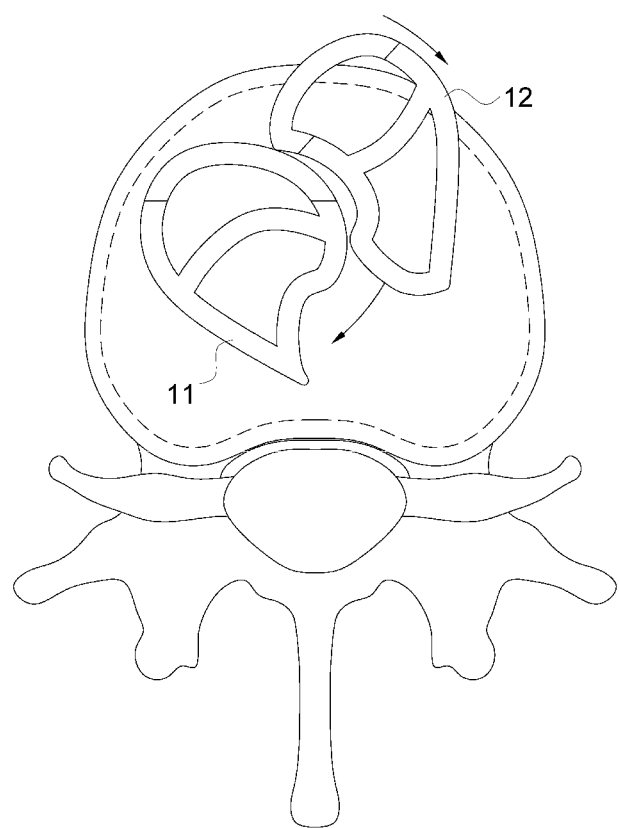
FIG. 7 is a plan view illustrating a state in which the following insertion portion is moved to correspond to the leading insertion portion according to one embodiment of the present invention.

FIG. 7 is a plan view illustrating a state in which the following insertion portion 12 is moved to correspond to the leading insertion portion 11 according to one embodiment of the present invention.

As the following insertion portion 12 is inserted, the second concave portion 121 comes into contact with the first convex portion 111 and moves along the first convex portion 111 so that the second convex portion 122 is guided to a position of the first concave portion 112.

Figure 8:
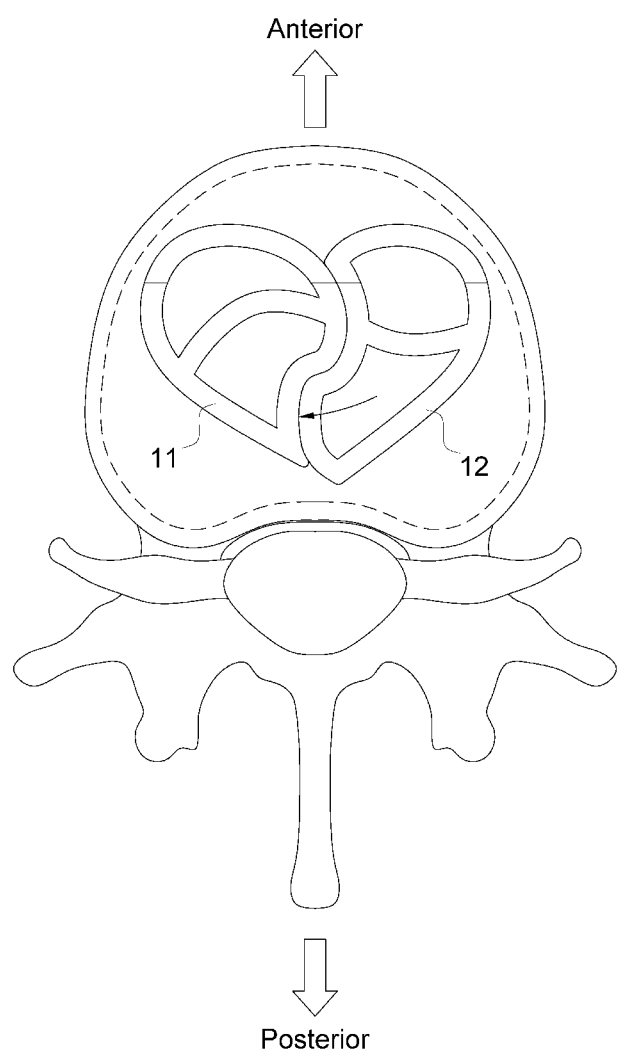
FIG. 8 is a plan view illustrating a state in which the following insertion portion is in position between the vertebrae according to one embodiment of the present invention.

FIG. 8 is a plan view illustrating a state in which the following insertion portion 12 is in position between the vertebrae V according to one embodiment of the present invention.

The first convex portion 111 and the second concave portion 121 are coupled to correspond to each other and the first concave portion 112 and the second convex portion 122 are coupled to correspond to each other so that the following insertion portion 12 is in position in the one direction of the leading insertion portion 11.

As described above, because the cage 10 according to the present invention is inserted in a separated form as the leading insertion portion 11 and the following insertion portion 12, it is easy to perform insertion surgery. Also, the cage 10 is easily combined through correspondence between the first curved surface 110 provided on the leading insertion portion 11 and the second curved surface 120 provided on the following insertion portion 12.

Figure 9:
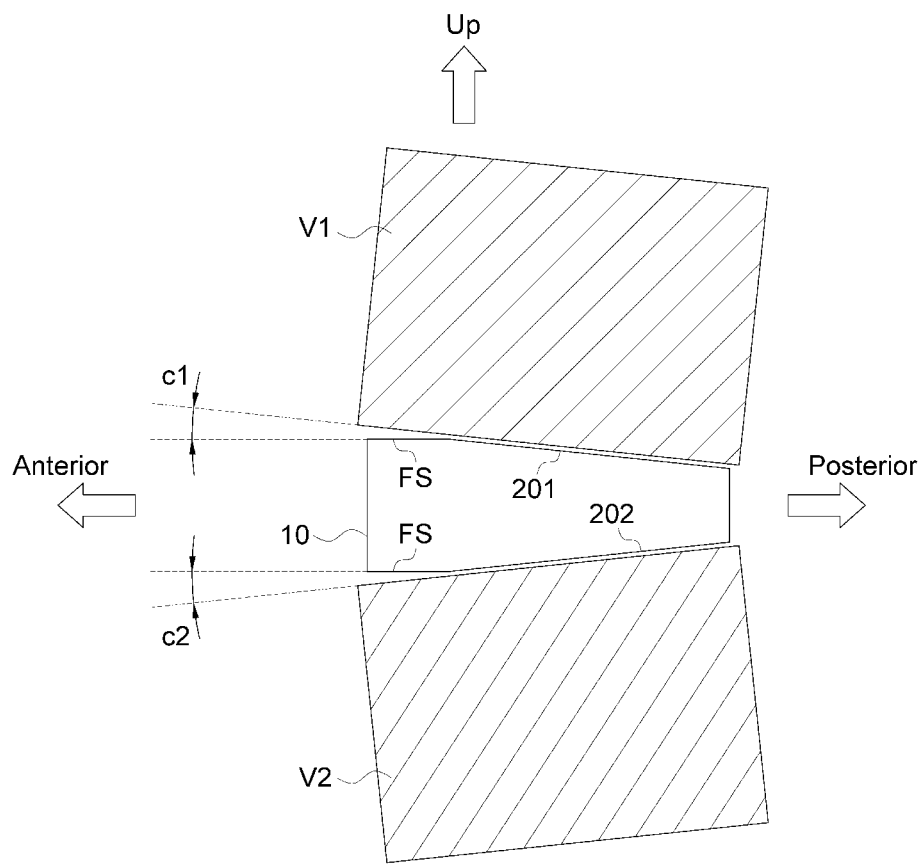
FIG. 9 is a side view illustrating a state in which the cage is inserted between the vertebrae according to one embodiment of the present invention.

FIG. 9 is a side view illustrating a state in which the cage 10 is inserted between the vertebrae according to one embodiment of the present invention. The upper vertebra V1 and the lower vertebra V2 form a certain angle with respect to horizontal according to an anterior curve formed by the spine in a normal condition. Hereinafter, an angle between the upper vertebra V1 and horizontal will be referred to as an upper angle c1, and an angle between the lower vertebra V2 and horizontal will be referred to as a lower angle c2.

According to the present invention, an upper inclined surface 201 and a lower inclined surface 202 may be provided on the upper surface and lower surface of the cage 10, and the respective inclined surfaces are provided to be in position when the cage 10 is inserted in an insertion direction Dl. In detail, when the cage 10 is in position, the upper inclined surface 201 corresponds to the lower surface of the upper vertebra V1 and the lower inclined surface 202 corresponds to the upper surface of the lower vertebra V2. That is, the upper inclined surface 201 of the cage is provided as an inclined surface at the upper angle c1 with respect to horizontal, and the lower inclined surface 202 of the cage is provided as an inclined surface at the lower angle c2 with respect to horizontal.

Figure 10:
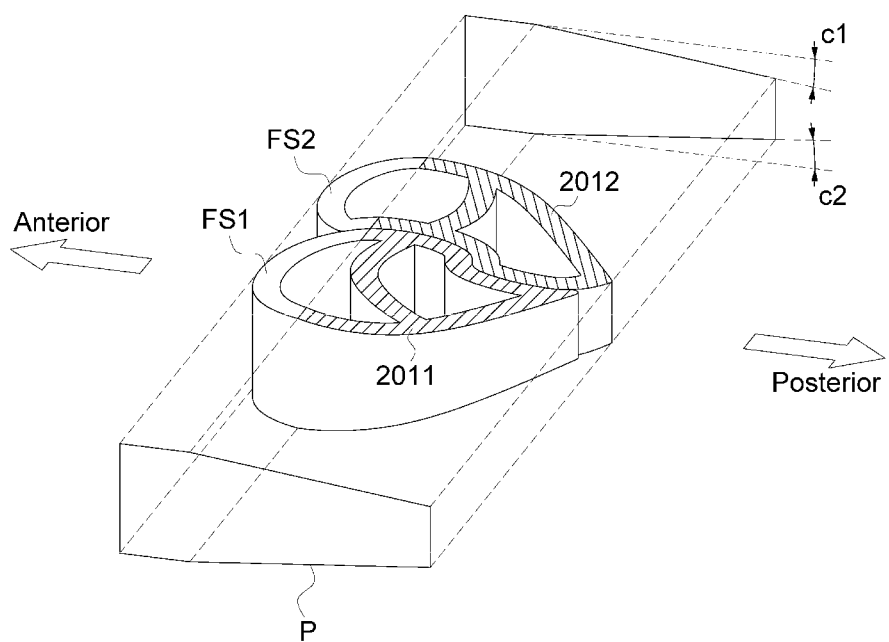
FIG. 10 is a perspective view illustrating an upper inclined surface of the cage according to one embodiment of the present invention.

FIG. 10 is a perspective view illustrating the upper inclined surface 201 of the cage 10 according to one embodiment of the present invention.

A figure P shown at the upper right and lower left of FIG. 10 is an outline of the cage 10 according to the present invention which is projected toward each side. A first upper inclined surface 2011 is formed on an upper surface of the leading insertion portion 11, and a second upper inclined surface 2012 is formed on an upper surface of the following insertion portion 12. As shown in FIG. 10, the first upper inclined surface 2011 and the second upper inclined surface 2012 are provided as grades corresponding to the upper angle c1 between the lower surface of the upper vertebra V1 and horizontal. Although not shown in FIG. 10, like the upper inclined surface 201, the lower inclined surface 202 is provided as a grade corresponding to the lower angle c2 between the upper surface of the lower vertebra V2 and horizontal. Accordingly, the cage 10 may be in position in the centrum space S.

Meanwhile, referring to FIG. 9, an inclined surface 200 may be formed in an area excluding a certain area FS in the front of the vertebrae V. Accordingly, a part corresponding to the certain area FS is provided horizontally and disperses a load applied to the front of the vertebrae V. Preferably, a boundary edge between the certain area FS and the inclined surface 200 is rounded to smoothly correspond to the vertebrae V and not to injure the upper vertebra V1 and the lower vertebra V2. In FIG. 10, a part of the leading insertion portion 11 corresponding to the certain area FS is shown as a first certain area FS1 and a part of the following insertion portion 12 corresponding to the certain area FS is shown as a second certain area FS2.

Figure 11:
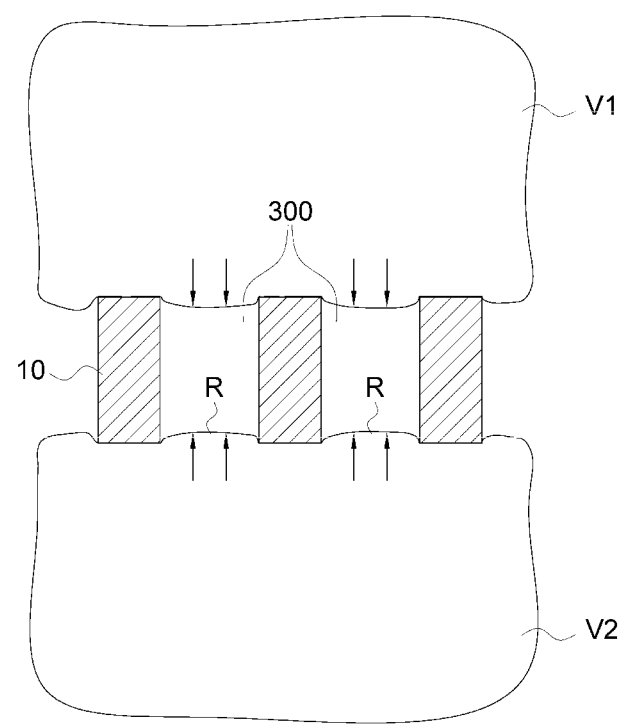
FIG. 11 is a vertical cross-sectional view illustrating a growth space portion of the cage according to one embodiment of the present invention.

FIG. 11 is a vertical cross-sectional view illustrating a growth space portion 300 of the cage 10 according to one embodiment of the present invention. The cage 10 according to the present invention may include the growth space portion 300 to allow a growing vertebral part R to penetrate and be fixed to the growth space portion. In detail, the growth space portion 300 is formed of recessed parts of the upper surface and lower surface of the cage 10, and the upper vertebra V1 and the lower vertebra V2 which are in contact with the cage 10 grow and penetrate the growth space portion 300. Also, the growth space portion 300 may be opened to pass through the upper surface and lower surface of the cage 10. The embodiment will be described on the basis that the growth space portion 300 is opened to pass through the upper surface and lower surface of the cage 10.

The upper vertebra V1 and the lower vertebra V2 are supported by the cage 10 while parts corresponding to the growth space portion 300 grow R to penetrate toward the inside of the cage 10 through the growth space portion 300. That is, in comparison to the parts supported by the cage 10, the upper vertebra V1 and the lower vertebra V2 grow R through the growth space portion 300 so that the upper vertebra V1 and the lower vertebra V2 are fused. Accordingly, there is an effect that the upper vertebra V1, the lower vertebra V2, and the cage 10 are firmly coupled to one another. Also, since the growth space portion 300 passing through the upper surface and lower surface of the cage 10 is provided, a load applied to the cage 10 is dispersed along a perimeter of the growth space portion 300, and thus there is an effect of increasing the strength of the cage 10.

Also, a plurality of such growth space portions 300 may be provided to increase the strength of the cage 10. A basis of the description will be that each of the leading insertion portion 11 and the following insertion portion 12 includes the plurality of growth space portions 300. Since the plurality of growth space portions 300 each disperse the load, the strength increases in comparison to a case in which a single growth space portion 300 is formed.

Meanwhile, during a process in which the cage 10 is inserted, it is difficult for the operating surgeon to see whether the cage 10 is in position through direct observation with the naked eye. To remedy this, the cage 10 according to the present invention may further include a position detection portion 400. In detail, one or more of such position detection portions 400 may be provided in parts inside the cage 10 which are designated in advance and are sensed using a position readout device to provide the operating surgeon with information on an accurate insertion position. For example, when the position readout device using a scanning means such as X-rays is provided, the position detection portions 400 include a metal material so that positions of the position detection portions 400 are accurately seen using X-rays and thus it is possible to accurately recognize the position of the cage 10.

Figure 12:
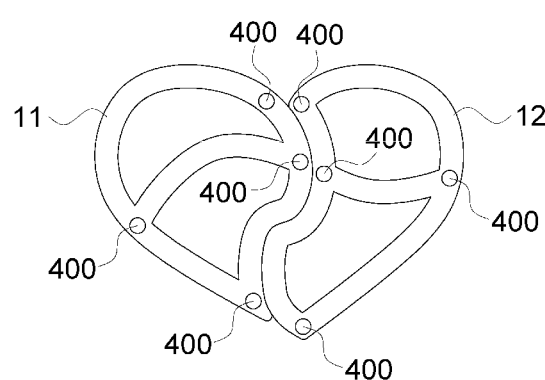
FIG. 12 is a plan view illustrating a position detection portion according to one embodiment of the present invention.
Figure 13:
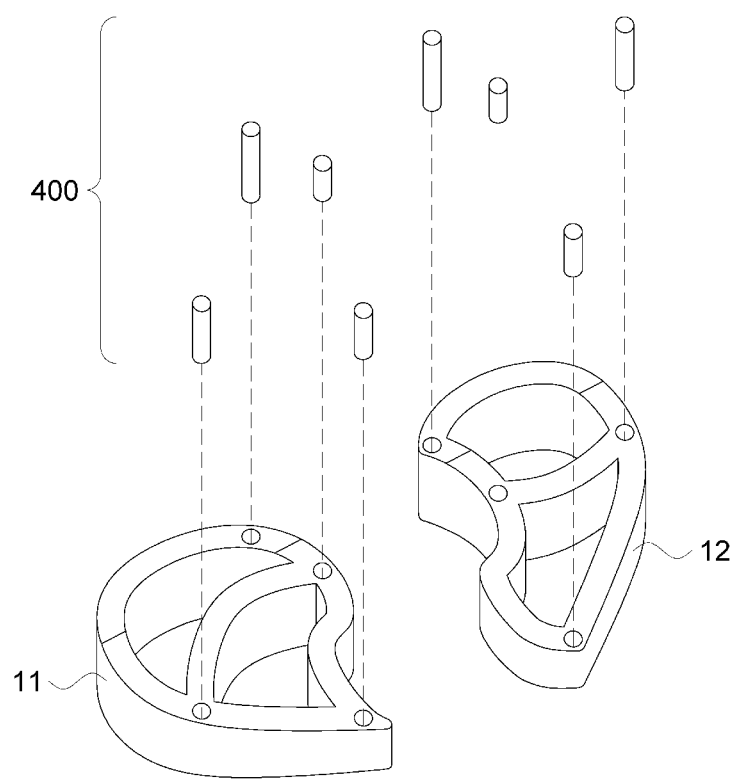
FIG. 13 is a perspective view illustrating the position detection portion according to one embodiment of the present invention.

FIG. 12 is a plan view illustrating the position detection portions 400 according to one embodiment of the present invention, and FIG. 13 is a perspective view illustrating the position detection portions 400 according to one embodiment of the present invention. According to the embodiment, the position detection portions 400 may be provided to have a column shape toward an upper side and lower side of the cage 10.

Also, the position detection portions 400 according to the present invention may be provided to have a column shape passing through the upper surface and lower surface of the cage 10.

Figure 14:
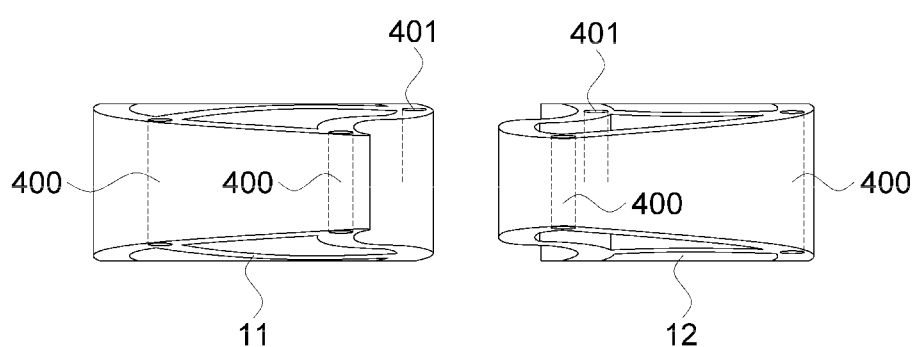
FIG. 14 is a rear view illustrating the position detection portion according to one embodiment of the present invention.

FIG. 14 is a rear view illustrating the position detection portions 400 according to one embodiment of the present invention. Since the respective position detection portions 400 are provided to pass through the upper surface and lower surface of the cage 10, even when the upper surface and lower surface of the cage 10 are not directly shown on the position readout device, the upper surface and lower surface of the cage 10 may be recognized by the position detection portions 400.

Also, when the cage 10 is not directly shown on the position readout device, it may be difficult to distinguish the top and bottom of the cage 10. To remedy this, one or more top/bottom detection portions 401 may be provided. In detail, the position detection portions 400 have a length passing through the upper surface and lower surface of the cage 10, and the top/bottom detection portions 401 have a length shorter than that of the position detection portions 400 to pass through only one of the upper surface and lower surface of the cage 10. Accordingly, the upper side and lower side of the cage 10 are asymmetrical due to the top/bottom detection portions 401, and the upper side and the lower side of the cage 10 may be distinguished from each other through the asymmetry of the position detection portions 400 seen on the position readout device. The embodiment has been described on the basis that the top/bottom detection portions 401 pass through only the upper surface of the cage 10.

Figure 15:
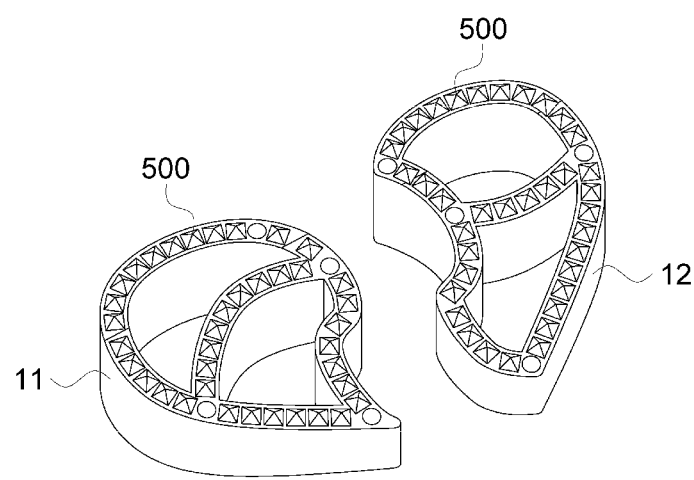
FIG. 15 is a perspective view illustrating protrusions according to one embodiment of the present invention.

Meanwhile, the cage 10 according to the present invention may further include a plurality of protrusions 500 provided on the upper surface and lower surface. FIG. 15 is a perspective view illustrating the protrusions 500 according to one embodiment of the present invention. Since the plurality of protrusions 500 formed to protrude from the upper surface and lower surface of the cage 10 are provided, coupling between the upper vertebra V1 and the lower vertebra V2 may be firm. Since the cage 10 is fixed between the upper vertebra V1 and the lower vertebra V2 by the protrusions 500 in addition to being fixed through the growth space portions 300, the cage 10 may be prevented from being separated and may stably support the upper vertebra V1 and the lower vertebra V2.

The above exemplary embodiments of the present invention have been disclosed for the purpose of exemplification, and it should be noted that a variety of modifications, changes, and additions can be made by those of ordinary skill in the art without departing from the concept and scope of the present invention and the modifications, changes, and additions are included in the scope of the claims.

Since a variety of substitution, modifications, and changes may be made by those of ordinary skill in the art without departing from the technical concept of the present invention, the present invention is not limited by the above embodiments or the attached drawings.

The invention claimed is:

1. A cage, which is configured to be inserted between a plurality of vertebrae, the cage comprising:
    a leading insertion coupler configured to be inserted from a front of the plurality of vertebrae and to be in position between the plurality of vertebrae; and
    a following insertion coupler configured to be combined with one surface of the leading insertion coupler and to be in position between the plurality of vertebrae,
    wherein the leading insertion coupler and the following insertion coupler, respectively, comprise one or more position detection portions disposed in inner parts and configured to detect positions of the leading insertion coupler and the following insertion coupler,
    wherein the leading insertion coupler includes a first upper surface and a first lower surface, and the following insertion coupler includes a second upper surface and a second lower surface,
    wherein the one or more position detection portions have a length to pass through the first and second upper surfaces and the first and second lower surfaces,
    wherein one or more of the one or more position detection portions are top/bottom detection portions, and
    wherein the top/bottom detection portions have a length smaller than the length of the position detection portions to pass through one of the first and second upper surfaces and the first and second lower surfaces.

2. The cage of claim 1, further comprising:
    a first curved surface provided on the leading insertion coupler in one direction; and
    a second curved surface provided on the following insertion coupler in another different direction.

3. The cage of claim 2, wherein the first curved surface comprises a first convex protrusion formed to protrude in the one direction and a first concave recess formed adjacent to the first convex protrusion, and
    wherein the second curved surface (120) comprises a second concave recess and a second convex protrusion which correspond to the first convex protrusion and the first concave recess, respectively.

4. The cage of claim 3, wherein, when the leading insertion coupler and the following insertion coupler are combined with each other, the first curved surface and the second curved surface come into surface contact with each other to correspond to each other.

5. The cage of claim 4, wherein the following insertion coupler is configured to be inserted to allow the second concave recess to move along the first curved surface so that the second convex protrusion is guided to the first concave recess.

6. The cage of claim 1, wherein the leading insertion coupler and the following insertion coupler each have a cross-sectional shape in which a width of one end in an insertion direction is smaller than a width of another end.

7. The cage of claim 1, wherein the leading insertion coupler and the following insertion coupler include inclined surfaces on the first and second upper surfaces and the first and second lower surfaces, and the inclined surfaces are disposed to have an upper angle and a lower angle with respect to the plurality of vertebrae while the leading insertion coupler and the following insertion coupler are in position between the plurality of vertebrae.

8. The cage of claim 1, wherein the leading insertion coupler and the following insertion coupler include growth space portions to allow growing vertebral parts to penetrate and be fixed to the growth space portions.

9. The cage of claim 1, wherein the first and second upper surfaces and the first and second lower surfaces are opened and thus growth space portions are formed to provide a space in which an upper vertebra and a lower vertebra grow to be fused.

\* \* \* \* \*